United States Patent
Turba et al.

(10) Patent No.: US 9,574,233 B2
(45) Date of Patent: Feb. 21, 2017

(54) METHOD FOR DETECTING THE SYNTHESIS AND/OR AMPLIFICATION OF A TARGET NUCLEIC ACID SEQUENCE

(71) Applicant: GENEFAST S.R.L., Bazzano (IT)

(72) Inventors: Maria Elena Turba, Forli' (IT); Elisa Zambon, Fiumicello (IT)

(73) Assignee: Genefast S.R.L., Bazzano (BO) (IT)

( * ) Notice: Subject to any disclaimer, the term of this patent is extended or adjusted under 35 U.S.C. 154(b) by 345 days.

(21) Appl. No.: 14/361,049

(22) PCT Filed: Nov. 29, 2012

(86) PCT No.: PCT/IB2012/056825
§ 371 (c)(1),
(2) Date: May 28, 2014

(87) PCT Pub. No.: WO2013/080154
PCT Pub. Date: Jun. 6, 2013

(65) Prior Publication Data
US 2014/0329232 A1 Nov. 6, 2014

(30) Foreign Application Priority Data

Nov. 29, 2011 (IT) .............................. MI2011A2177

(51) Int. Cl.
*C12P 19/34* (2006.01)
*C12Q 1/68* (2006.01)
*C12Q 1/70* (2006.01)

(52) U.S. Cl.
CPC ............. *C12Q 1/6844* (2013.01); *C12Q 1/689* (2013.01); *C12Q 1/6846* (2013.01); *C12Q 1/70* (2013.01); *C12Q 1/701* (2013.01); *C12Q 2600/16* (2013.01)

(58) Field of Classification Search
USPC ................................................ 435/6.12, 91.2
See application file for complete search history.

(56) References Cited

U.S. PATENT DOCUMENTS

2011/0294112 A1* 12/2011 Bearinger ............ C12Q 1/6844
435/5

OTHER PUBLICATIONS

Goto et al.,"Colorimetric detection of loop-mediated isothermal amplification reaction by using hydroxyl naphthol blue," BioTechniques, vol. 46, No. 3, 2009, pp. 167-172.
Goto et al., "Rapid detection of *Pseudomonas aeruginosa* in mouse feces by colorimetric loop-mediated isothermal amplification," Journal of Microbiological Methods 31 (2010) pp. 247-252.
Wastling et al., "Lamp for Human African Trypanosomiasis: A Comparative Study of Detection Formats," PLoS, vol. 4, Issue 11, Nov. 2010.
Zhang et al., "Direct DNA Amplification from Crude Clinical Samples Using a PCR Enhancer Cocktail and Novel Mutants of Taq," Journal of Molecular Diagnostics, vol. 12, No. 2, Mar. 2010, pp. 152-161.
International Search Report and Written Opinion for PCT/IB2012/056825 mailed Feb. 18, 2013.

* cited by examiner

*Primary Examiner* — Kenneth Horlick
(74) *Attorney, Agent, or Firm* — RatnerPrestia

(57) ABSTRACT

The present invention relates to a method for the detection of nucleic acid synthesis and/or amplification, characterized in that the method includes adding at least one colorimetric metal indicator and at least one bland magnesium chelator to a reaction mixture for nucleic acid amplification. The present invention further relates to a kit for carrying out such a method and to the use thereof in the health, food and agricultural or veterinary fields.

14 Claims, 3 Drawing Sheets

SEQUENCE LISTING

<160> NUMBER OF SEQ ID NOS: 42

<210> SEQ ID NO 1
<211> LENGTH: 24
<212> TYPE: DNA
<213> ORGANISM: Artificial
<220> FEATURE:
<223> OTHER INFORMATION: primer F3 - candidatus Mycoplasma haemominutum

<400> SEQUENCE: 1
ttaccgaggc ttgtaatctt ttgc                                          24

<210> SEQ ID NO 2
<211> LENGTH: 25
<212> TYPE: DNA
<213> ORGANISM: Artificial
<220> FEATURE:
<223> OTHER INFORMATION: primer B3 - candidatus Mycoplasma haemominutum

<400> SEQUENCE: 2
tgagataggt tttcggtgat tagct                                         25

<210> SEQ ID NO 3
<211> LENGTH: 49
<212> TYPE: DNA
<213> ORGANISM: Artificial
<220> FEATURE:
<223> OTHER INFORMATION: primer FIP - candidatus Mycoplasma haemominutum

<400> SEQUENCE: 3
cgctcgttac gggacttaac caaactggag gttatcagaa tgacaggtg               49

<210> SEQ ID NO 4
<211> LENGTH: 49
<212> TYPE: DNA
<213> ORGANISM: Artificial
<220> FEATURE:
<223> OTHER INFORMATION: primer BIP - candidatus Mycoplasma haemominutum

<400> SEQUENCE: 4
tcgtaagata taggaaggct ggggccatta tgcctaccat tgtagcacg               49

<210> SEQ ID NO 5
<211> LENGTH: 19
<212> TYPE: DNA
<213> ORGANISM: Artificial
<220> FEATURE:
<223> OTHER INFORMATION: primer LF - candidatus Mycoplasma haemominutum

<400> SEQUENCE: 5
agctgacgac agccatgca                                                19

<210> SEQ ID NO 6
<211> LENGTH: 23
<212> TYPE: DNA
<213> ORGANISM: Artificial
<220> FEATURE:
<223> OTHER INFORMATION: primer LB - candidatus Mycoplasma haemominutum

<400> SEQUENCE: 6
caagtcatca tgccccttat gcc                                           23

<210> SEQ ID NO 7
<211> LENGTH: 20
<212> TYPE: DNA
<213> ORGANISM: Artificial

```
<220> FEATURE:
<223> OTHER INFORMATION: Primer F3 - candidatus Mycoplasma turicensis

<400> SEQUENCE: 7
aggcgaaaac ttaggccatt                                              20

<210> SEQ ID NO 8
<211> LENGTH: 20
<212> TYPE: DNA
<213> ORGANISM: Artificial
<220> FEATURE:
<223> OTHER INFORMATION: primer B3 - candidatus Mycoplasma turicensis

<400> SEQUENCE: 8
tgttccacca cttgttcagg                                              20

<210> SEQ ID NO 9
<211> LENGTH: 46
<212> TYPE: DNA
<213> ORGANISM: Artificial
<220> FEATURE:
<223> OTHER INFORMATION: Primer FIP - candidatus Mycoplasma turicensis

<400> SEQUENCE: 9
acggtgtgga ctactggggt attttacgct taggcttgaa agtgtg                 46

<210> SEQ ID NO 10
<211> LENGTH: 47
<212> TYPE: DNA
<213> ORGANISM: Artificial
<220> FEATURE:
<223> OTHER INFORMATION: primer BIP - candidatus Mycoplasma turicensis

<400> SEQUENCE: 10
tcggcgttgt agcttacgtg ttttttccc cgtcaattcc tttgagt                 47

<210> SEQ ID NO 11
<211> LENGTH: 19
<212> TYPE: DNA
<213> ORGANISM: Artificial
<220> FEATURE:
<223> OTHER INFORMATION: primer LF - candidatus Mycoplasma turicensis

<400> SEQUENCE: 11
tctaatccca tttgctacc                                               19

<210> SEQ ID NO 12
<211> LENGTH: 20
<212> TYPE: DNA
<213> ORGANISM: Artificial
<220> FEATURE:
<223> OTHER INFORMATION: Primer LB - Candidatus Mycoplasma turicensis

<400> SEQUENCE: 12
cgcctgggta gtacatatgc                                              20

<210> SEQ ID NO 13
<211> LENGTH: 24
<212> TYPE: DNA
<213> ORGANISM: Artificial
<220> FEATURE:
<223> OTHER INFORMATION: Primer F3 - Mycoplasma haemofelis

<400> SEQUENCE: 13
atgaatgtat ttttaaatgc ccac                                         24
```

<210> SEQ ID NO 14
<211> LENGTH: 20
<212> TYPE: DNA
<213> ORGANISM: Artificial
<220> FEATURE:
<223> OTHER INFORMATION: Primer B3 - Mycoplasma haemofelis

<400> SEQUENCE: 14
aaggatggga tcacgtcaag                                                 20

<210> SEQ ID NO 15
<211> LENGTH: 46
<212> TYPE: DNA
<213> ORGANISM: Artificial
<220> FEATURE:
<223> OTHER INFORMATION: primer FIP - Mycoplasma haemofelis

<400> SEQUENCE: 15
accatcgctg gtttgcaaca cattttgtca tcatgcccct tatgcc                    46

<210> SEQ ID NO 16
<211> LENGTH: 43
<212> TYPE: DNA
<213> ORGANISM: Artificial
<220> FEATURE:
<223> OTHER INFORMATION: Primer BIP - Mycoplasma haemofelis

<400> SEQUENCE: 16
tcggatagga ggctgcaatt cgcccccgat atagctgaca cgg                       43

<210> SEQ ID NO 17
<211> LENGTH: 17
<212> TYPE: DNA
<213> ORGANISM: Artificial
<220> FEATURE:
<223> OTHER INFORMATION: Primer LF - Mycoplasma haemofelis

<400> SEQUENCE: 17
gcacgtttgc agcccaa                                                    17

<210> SEQ ID NO 18
<211> LENGTH: 23
<212> TYPE: DNA
<213> ORGANISM: Artificial
<220> FEATURE:
<223> OTHER INFORMATION: primer LB - Mycoplasma haemofelis

<400> SEQUENCE: 18
ctccttgaag ttggaatcac tag                                             23

<210> SEQ ID NO 19
<211> LENGTH: 18
<212> TYPE: DNA
<213> ORGANISM: Artificial
<220> FEATURE:
<223> OTHER INFORMATION: primer F3 - Listeria monocytogenes

<400> SEQUENCE: 19
agccgtggat gttatcgt                                                   18

<210> SEQ ID NO 20
<211> LENGTH: 19
<212> TYPE: DNA
<213> ORGANISM: Artificial
<220> FEATURE:
<223> OTHER INFORMATION: Primer B3 - Listeria monocytogenes

<400> SEQUENCE: 20
gaaaagctta ttcatgggg                                                    19

<210> SEQ ID NO 21
<211> LENGTH: 45
<212> TYPE: DNA
<213> ORGANISM: Artificial
<220> FEATURE:
<223> OTHER INFORMATION: Primer FIP - Listeria monocytogenes

<400> SEQUENCE: 21
gtacgtggaa gggagatacc cttttttgat tgctctggtt acact                      45

<210> SEQ ID NO 22
<211> LENGTH: 46
<212> TYPE: DNA
<213> ORGANISM: Artificial
<220> FEATURE:
<223> OTHER INFORMATION: primer BIP - Listeria monocytogenes

<400> SEQUENCE: 22
tgaatctcaa gcaaaacctg gttttcaac gtgagaaatt ccgcta                      46

<210> SEQ ID NO 23
<211> LENGTH: 20
<212> TYPE: DNA
<213> ORGANISM: Artificial
<220> FEATURE:
<223> OTHER INFORMATION: Primer LF - Listeria monocytogenes

<400> SEQUENCE: 23
gctttagcaa atacatattt                                                   20

<210> SEQ ID NO 24
<211> LENGTH: 23
<212> TYPE: DNA
<213> ORGANISM: Artificial
<220> FEATURE:
<223> OTHER INFORMATION: Primer LB - Listeria monocytogenes

<400> SEQUENCE: 24
gatttagtat tcttcgacta tgg                                               23

<210> SEQ ID NO 25
<211> LENGTH: 21
<212> TYPE: DNA
<213> ORGANISM: Artificial
<220> FEATURE:
<223> OTHER INFORMATION: Primer F3 - CPV/FPV

<400> SEQUENCE: 25
caggtgatga atttgctaca g                                                 21

<210> SEQ ID NO 26
<211> LENGTH: 19
<212> TYPE: DNA
<213> ORGANISM: Artificial
<220> FEATURE:
<223> OTHER INFORMATION: Primer B3 - CPV/FPV

<400> SEQUENCE: 26
tcctgctgca ataggtgtt                                                    19

<210> SEQ ID NO 27

```
<211> LENGTH: 48
<212> TYPE: DNA
<213> ORGANISM: Artificial
<220> FEATURE:
<223> OTHER INFORMATION: Primer FIP - CPV/FPV

<400> SEQUENCE: 27
ccaaagttag tacctccttc agcttttac aaatagagca ttgggctt                    48

<210> SEQ ID NO 28
<211> LENGTH: 49
<212> TYPE: DNA
<213> ORGANISM: Artificial
<220> FEATURE:
<223> OTHER INFORMATION: Primer BIP - CPV/FPV

<400> SEQUENCE: 28
gacgtggtgt aactcaaatg ggaattttgt gcactataac caacctcag                  49

<210> SEQ ID NO 29
<211> LENGTH: 25
<212> TYPE: DNA
<213> ORGANISM: Artificial
<220> FEATURE:
<223> OTHER INFORMATION: primer LF - CPV/FPV

<400> SEQUENCE: 29
gaggcaaaga atttagaaat ggtgg                                            25

<210> SEQ ID NO 30
<211> LENGTH: 25
<212> TYPE: DNA
<213> ORGANISM: Artificial
<220> FEATURE:
<223> OTHER INFORMATION: primer LB - CPV/FPV

<400> SEQUENCE: 30
actgaagcta ctattatgag accag                                            25

<210> SEQ ID NO 31
<211> LENGTH: 21
<212> TYPE: DNA
<213> ORGANISM: Artificial
<220> FEATURE:
<223> OTHER INFORMATION: primer F3 - Pseudomonas fluorescens

<400> SEQUENCE: 31
aagcacttta agttgggagg a                                                21

<210> SEQ ID NO 32
<211> LENGTH: 19
<212> TYPE: DNA
<213> ORGANISM: Artificial
<220> FEATURE:
<223> OTHER INFORMATION: primer B3 - Pseudomonas fluorescens

<400> SEQUENCE: 32
acgcatttca ccgctacac                                                   19

<210> SEQ ID NO 33
<211> LENGTH: 50
<212> TYPE: DNA
<213> ORGANISM: Artificial
<220> FEATURE:
<223> OTHER INFORMATION: primer FIP - Pseudomonas fluorescens

<400> SEQUENCE: 33
```
ttacgcccag taattccgat taacgttttg acagaataag caccggctaa        50

<210> SEQ ID NO 34
<211> LENGTH: 48
<212> TYPE: DNA
<213> ORGANISM: Artificial
<220> FEATURE:
<223> OTHER INFORMATION: primer BIP - Pseudomonas fluorescens

<400> SEQUENCE: 34
ctcaacctgg gaactgcatt caattttagg aaattccacc accctcta          48

<210> SEQ ID NO 35
<211> LENGTH: 20
<212> TYPE: DNA
<213> ORGANISM: Artificial
<220> FEATURE:
<223> OTHER INFORMATION: Primer LF - Pseudomonas fluorescens

<400> SEQUENCE: 35
ctgtattacc gcggctgctg                                         20

<210> SEQ ID NO 36
<211> LENGTH: 21
<212> TYPE: DNA
<213> ORGANISM: Artificial
<220> FEATURE:
<223> OTHER INFORMATION: primer LB - Pseudomonas fluorescens

<400> SEQUENCE: 36
aactgtcgag ctagagtatg g                                       21

<210> SEQ ID NO 37
<211> LENGTH: 19
<212> TYPE: DNA
<213> ORGANISM: Artificial
<220> FEATURE:
<223> OTHER INFORMATION: primer F3 - Leptospira interrogans

<400> SEQUENCE: 37
gtggaattcc aggtgtagc                                          19

<210> SEQ ID NO 38
<211> LENGTH: 20
<212> TYPE: DNA
<213> ORGANISM: Artificial
<220> FEATURE:
<223> OTHER INFORMATION: Primer B3 - Leptospira interrogans

<400> SEQUENCE: 38 ggttttcgc gtatcatcga                                          20

<210> SEQ ID NO 39
<211> LENGTH: 44
<212> TYPE: DNA
<213> ORGANISM: Artificial
<220> FEATURE:
<223> OTHER INFORMATION: Primer FIP - Leptospira interrogans

<400> SEQUENCE: 39
accggggtat ctaatcccgt ttttttgct ggcctaaaac tgac              44

<210> SEQ ID NO 40
<211> LENGTH: 46
<212> TYPE: DNA

-continued

```
<213> ORGANISM: Artificial
<220> FEATURE:
<223> OTHER INFORMATION: primer BIP - Leptospira interrogans

<400> SEQUENCE: 40
agttgttggg ggttttaacc cttttttttc actcttgcga gcatag                  46

<210> SEQ ID NO 41
<211> LENGTH: 19
<212> TYPE: DNA
<213> ORGANISM: Artificial
<220> FEATURE:
<223> OTHER INFORMATION: Primer LF - Leptospira interrogans

<400> SEQUENCE: 41
actacccacg ctttcgtgc                                                19

<210> SEQ ID NO 42
<211> LENGTH: 21
<212> TYPE: DNA
<213> ORGANISM: Artificial
<220> FEATURE:
<223> OTHER INFORMATION: primer LB - Leptospira interrogans

<400> SEQUENCE: 42
acggattaag tagaccgcct g                                             21
```

METHOD FOR DETECTING THE SYNTHESIS AND/OR AMPLIFICATION OF A TARGET NUCLEIC ACID SEQUENCE

This application is the U.S. National Phase Application of PCT/IB2012/056825, filed Nov. 29, 2012, which claims priority to Italian Patent Application No. MI2011A002177, filed Nov. 29, 2011, the contents of such applications being incorporated by reference herein.

The present invention relates to a method for the detection of nucleic acid synthesis and/or amplification.

The best known technique for amplifying nucleic acids is based on an enzymatic reaction named Polymerase Chain Reaction, commonly known under the acronym PCR.

PCR reproduces in vitro the synthesis phase of the cellular cycle, during which the genetic material is duplicated in order to be equally distributed to the daughter cells.

More particularly, a classical PCR protocol includes a step of nucleic acid denaturation (performed at a temperature varying in the range 95 to 99° C.) before the various amplification cycles. This step is necessary since the polymerase, i.e. the enzyme responsible for the nucleic acid amplification, uses a single-stranded nucleic acid as a template for the synthesis of the complementary sequence. More particularly, the polymerase synthesises the new strand of nucleic acid by sequentially inserting the complementary nucleotides to those present on the template strand starting from small fragments of nucleic acid acting as primers.

At each cycle, the nucleic acid is denatured at high temperature (denaturation step). Subsequently, the temperature is lowered to such a value as to allow the primers to bind to the complementary regions of the template nucleic acid (annealing step). Eventually, the polymerisation step takes place, i.e. the polymerase synthesises the new chain of nucleic acid starting from the primer as described above. This denaturation-annealing-polymerisation cycle is iterated several times in order to amplify even very low amounts of template nucleic acid. The selected polymerase is heat-resistant since it is to be subjected to high temperatures for a long time.

The need to denature the nucleic acid in order to allow amplifying same obliges to use, for the execution of PCR, a thermal cycler enabling operation at different temperatures during the different steps of the process and a fast transition from one temperature to another.

This constraint results in PCR being a technique hardly utilisable for the improvised surveys, i.e. for those tests that are to be performed in simple and quick manner in the field in order to take the most appropriate decisions in timely manner.

A very good technique that dispenses the nucleic acid amplification protocols with the use of a thermal cycler is the loop mediated isothermal amplification, in short LAMP.

LAMP allows isothermal amplification of nucleic acids. In other words, during the whole LAMP reaction, temperature is constantly kept in the range 60 to 65° C. The constant temperature conditions allow executing the whole LAMP amplification protocol in a thermostated bath, in a stove or in a thermal block. In this way, a nucleic acid amplification protocol is available, which is wholly free from the use of the sophisticate and complex thermal cycler required to perform PCR.

In this respect, LAMP appears as a selectable methodology for the nucleic acid amplification processes performed in the field and in a manner wholly independent of the laboratory. That is, LAMP seems to be a particularly suitable methodology for the analyses known as "point-of-care testing". Indeed, this kind of analyses, being performed in the field in improvised manner by staff that needs not to be a skilled staff, requires very versatile and easily implementable techniques.

An aspect of the nucleic acid amplification techniques like PCR and LAMP, which at present still is problematic and hence limiting, especially for the execution of point-of-care tests, concerns the step of detecting the possibly amplified nucleic acid.

Usually, a nucleic acid amplified by means of PCR or by means LAMP can be visualised through gel electrophoresis performed in the presence of intercalating agents. Intercalating agents are molecules capable of emitting fluorescence when they are excited by UV radiation. Intercalating agents, such as for instance ethidium bromide, act by entering the double helix of the amplified nucleic acid, which can thus be visualised by using UV radiation.

In the alternative, nucleic acid amplification can be monitored in real time (real-time analysis) by performing the amplification reaction in the presence of fluorescent precursors and by measuring the fluorescence emitted by the specimen under test by using suitable apparatuses. Lastly, in recent times, turbidimetry has become widespread as a method of detecting nucleic acid amplification (especially for LAMP-amplified nucleic acids).

The turbidimeter measures the increase in the turbidity of the reaction mixture occurring as the nucleic acid amplification reaction proceeds. The increase in the turbidity of the reaction mixture occurring upon nucleic acid amplification is related to the release of phosphate ions (coming from the nucleotides), which, in the presence of magnesium, precipitate as magnesium pyrophosphate and make the solution become turbid.

Yet, both the visualisation of the amplified nucleic acid by means of intercalating agents, and the real time visualisation by means of fluorescent molecules or the visualisation by means of the turbidimeter bind the execution of the nucleic acid amplification reaction to an ad hoc equipped structure (a laboratory or a facility) attended by skilled staff who is capable of managing the instrumentation and knows how to handle substances, such as the intercalating agents, which are dangerous for the public and environmental health.

Moreover, a further strongly limiting aspect related to the use of intercalating agents is that such agents are added to the mixture at the end of the amplification reaction and in the agarose gel, if the latter is used as the detection method. This entails opening the tubes where the reaction occurs and consequently, gives rise to a high risk of polluting the environment with the amplified nucleic acid (whether it is contained in the test specimens or it is contained in the positive control specimens).

Environmental contamination with nucleic acids can persist for very long periods notwithstanding the proper decontamination procedures are carried out. Moreover, the contaminations often give rises to false positives that may occur at even irregular intervals, even when the problem had apparently been solved. Under such a situation, in order to ensure contamination eradication, the only solution is to design again the test and to formulate again ex novo the components thereof (for instance, the primers used for amplification).

It is clear that this scenario, i.e. environmental contamination, is absolutely to be avoided, in particular during the setting up of diagnostic kits, since the validation step of a kit is an extremely expensive procedure.

Recently, in order to detect a LAMP-amplified DNA, Goto et al. have found that, by adding hydroxynaphthol blue (HNB) to the reaction mixture, it is possible to colorimetrically follow the nucleic acid amplification (Goto et al., Biotechniques (2009) Vol. 46: 167-172).

Hydroxynaphthol blue (HNB) is a metal ion indicator. As disclosed above, during the LAMP amplification reaction, magnesium concentration decreases since magnesium forms complexes with pyrophosphate and precipitates. The decrease in magnesium concentration accompanying nucleic acid amplification causes a change in the colour of a reaction mixture to which HNB has been added. In particular, the colour of the mixture passes from a deep blue tone to a light blue tone.

Yet, in the standard LAMP reaction conditions, such tone variations are difficult to be appreciated, especially when amplification is minimum (i.e. the specimen is weakly positive) and when the evaluating viewer is not skilled.

The detection of the amplification of a nucleic acid is thus a problem still to be solved.

In this context, the technical problem underlying the present invention is to provide a method for the detection of nucleic acid synthesis and/or amplification, which has a sensitivity, and hence a reliability of the results, improved over the prior art systems.

The Applicant has found a response to the technical problem stated above in a colorimetric method for the detection of the synthesis and/or amplification of a nucleic acid, wherein at least one colorimetric metal indicator and at least one magnesium chelator (preferably, a bland magnesium chelator) are added to a reaction mixture for nucleic acid amplification. Thereafter, the reaction mixture thus obtained is placed in contact with a specimen to be analysed in order to synthesise and/or amplify the nucleic acid possibly present in the specimen. Lastly, presumably at the end of the amplification process, there is checked whether a change in the starting colour occurred in the reaction mixture.

At the end of the amplification step, a definite change in the colour of the reaction mixture from a colour falling in the range of violet (for instance violet, lilac or magenta) to a colour falling in the range of blue (for instance, sky blue) is indicative of the presence of the target nucleic acid in the specimen being tested.

By applying the method of the present invention, the Applicant has surprisingly noticed a significant improvement in the colorimetric detection of the amplified nucleic acid with respect to the detection obtained by applying the prior art methods. In particular, the Applicant has realised that, by applying the method of the invention, the detection of nucleic acid amplification is more sensitive, i.e., it allows detecting lower concentrations of target nucleic acid, is robust, i.e. it is not affected by small variations in the method parameters, and hence it is more reliable than the methods the literature at present proposes to this aim.

The higher sensitivity of the method of the invention with respect to the prior art methods is due to the fact that the difference between a negative specimen and a weakly positive specimen can be seen by the naked eye as a definite colour change, whereas only a small change in a tone of the same colour (from deep blue to light blue) is obtained when applying the prior art methods. Actually, when a nucleic acid is amplified with the method of the invention, if nucleic acid amplification has occurred, the colour of the amplification reaction mixture passes from a colour falling in the range of violet (for instance violet, lilac or magenta) to a colour falling in the range of blue (for instance, sky blue). The colour difference is so evident that it can be readily appreciated also by a non-skilled viewer. This improvement in the visualisation of the amplified nucleic acid is possible only if at least one colorimetric metal indicator and at least one bland magnesium chelator are added in combination to the amplification reaction mixture.

The method of the present invention has proved more advantageous than the prior art method also from an economic standpoint. Actually, it works at lower nucleotide concentrations than the standard ones (it is known that the nucleotides are a very expensive starting material, which however is necessary in order to perform such methods). This allows reducing in non-negligible manner the costs associated with the application of the method, especially in mass screenings.

Finally, the Applicant has realised that the addition of the at least one bland magnesium chelator to a reaction mixture for nucleic acid amplification may, in some cases, favours the amplification reaction.

Hereinafter, the present invention will be described in detail also with the help of the accompanying Figures, in which.

Figure 1:
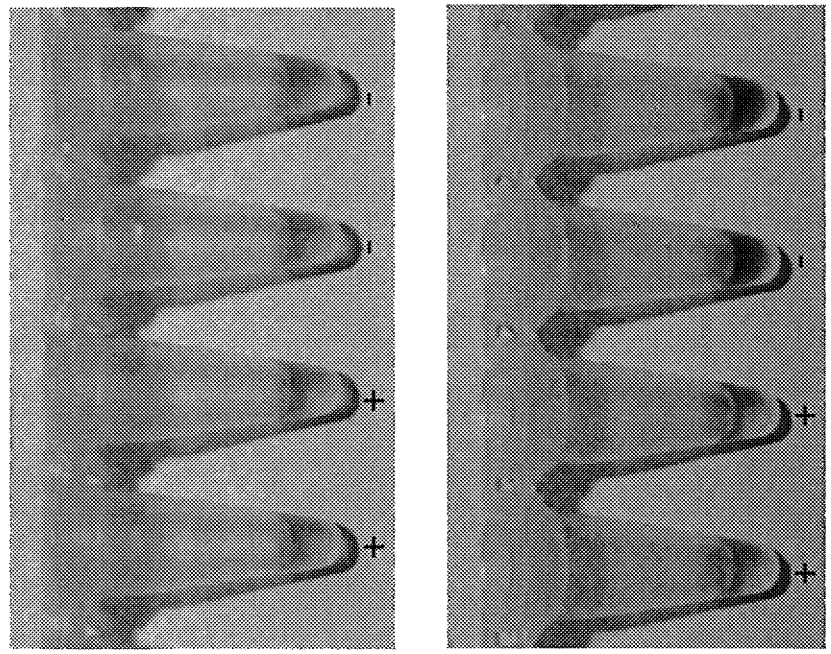
FIG. 1A shows the colour difference between a positive biological specimen (containing an amplified nucleic acid) and a negative biological specimen (not containing the nucleic acid) obtained by means of a prior art detection method in the absence of sodium citrate.
FIG. 1B shows the colour difference between a positive biological specimen (containing an amplified nucleic acid) and a negative biological specimen (not containing the nucleic acid) obtained by means of the method of the invention.

The present invention concerns a method of colorimetrically detecting nucleic acid synthesis and/or amplification of a, characterised in that said method comprises adding at least one colorimetric metal indicator and at least one bland magnesium chelator to a reaction mixture for nucleic acid amplification.

More particularly, the method of detecting the synthesis and/or amplification of a nucleic acid according to the present invention comprises the steps of:
(i) providing at least one set of primers designed for synthesising and/or amplifying in specific manner at least one region of the target nucleic acid;
(ii) combining the set of primers of step (i) with a reaction mixture for the amplification of a target nucleic acid, said mixture comprising at least one colorimetric metal indicator and at least one bland magnesium chelator;

(iii) placing the reaction mixture obtained from step (ii) in contact with a biological specimen so as to amplify at least one region of the target nucleic acid possibly present in the specimen; and (iv) verifying the possible change in the colour of the reaction mixture.

The addition of the combination of at least one colorimetric metal indicator and at least one bland magnesium chelator makes the reaction mixture colorimetrically sensitive to minimum amounts of amplified nucleic acid. Actually, by applying the method of the present invention, also small amounts of amplified nucleic acid are capable of causing a definite change in the colour of the reaction mixture. In the method according to the present invention, the colour of the mixture changes from a colour falling in the range of violet (for instance violet, lilac or magenta), to a colour falling in the range of blue (for instance sky blue). On the contrary, by applying the methods proposed by the prior art, the amplification of a nucleic acid makes the colour of the reaction mixture change from a deep blue to a sky blue. The method of the present invention allows considerably enhancing the colour differences between a positive specimen (i.e. a specimen in which a nucleic acid has been amplified) and a negative specimen (i.e. a specimen where no nucleic acid amplification occurred). Indeed, even a specimen which is only weakly positive (small amounts of amplified nucleic acid) is detectable by means of the method of the present invention. The combination of at least one bland magnesium chelator and at least one colorimetric metal indicator is essential for such a result.

A first aspect of the method of the present invention concerns the colorimetric metal indicator, which is preferably selected from among: hydroxynaphtol blue, eriochrome black T, 8-hydroxyquinoline+butylamide, titanium yellow, xylidyl blue, calmagite, magon, thymol blue, eriochrome cyanine R, alizarin S, o-cresolphthalein, 1,2,3-trihydroxyanthraquinone, leucoquinizarin, quinalizarin, p-nitrobenzene-azo-p-nitrobenzene-resorcinol, butylamide, chromotrope 2B, ammonia+phenolphthalein, alkaline hypoiodites, pentamethinedibarbituric acid and diphenylcarbazide.

Said indicator is preferably employed in a concentration varying from 0.05 to 0.2 mM and, more preferably from 0.1 to 0.15 mM.

The colorimetric metal indicator particularly preferred for the aims of the present invention is hydroxynaphtol blue.

A second aspect of the method of the present invention concerns the bland magnesium chelator, which is preferably selected from among: sodium citrate, acetic acid, ADP, aspartic acid, ATP, n-butyric acid, citric acid, cysteine, 3,4-dihydroxybenzoic acid, O,O-dimethylpurpurogallin, EDTA, EGTA, gluconic acid, glutamic acid, glutaric acid, glyceric acid, glycine, glycolic acid, glycylglycine, guanosine, B-hydroxybutyric acid, inosine triphosphate, lactic acid, malic acid, NTA, oxalic acid, polyphosphate, propionic acid, purine, salicylaldehyde, salicylic acid, succinic acid, tartaric acid, tetrametaphosphate, trimetaphosphate, triphosphate, uridine diphosphate.

Preferably said bland magnesium chelator is used in a concentration varying from 0.5 to 2 mM, more preferably from 0.8 to 1.2 mM.

The bland magnesium chelator particularly preferred for the aims of the present invention is sodium citrate.

In a preferred embodiment, hydroxynaphtol blue is used in combination with sodium citrate. The nucleic acid synthesised and/or amplified by the method according to the present invention is DNA and/or RNA. In case the nucleic acid to be amplified is an RNA molecule, the latter is preferably first subjected to reverse transcription by an enzyme such as the reverse transcriptase. The nucleic acid having undergone reverse transcription, or cDNA, is then amplified according to the method according to the present invention.

In the context of the present invention, the term "method of nucleic acid synthesis and/or amplification" is used to denote a methodology allowing multiplication of a determined fragment of a nucleic acid of interest. The method of nucleic acid synthesis and/or amplification preferred for the aims of the present invention is LAMP, PCR or variants thereof. Particularly preferred is the loop mediated isothermal amplification (LAMP).

The LAMP technique is a recently developed methodology of nucleic acid amplification (Notomi T et al., 2000).

The principles of the LAMP method are shortly described hereinbelow in order to make understanding of some preferred aspects of the method of the present invention easier.

The LAMP method is based on the use of a set of four primers (or oligonucleotides) specifically designed for a certain nucleic acid sequence, for instance a DNA molecule. Moreover, LAMP uses a thermophilic polymerase capable of synthesising and amplifying the target nucleic acid in isothermal conditions by means of "strand displacement".

The set of primers includes a pair of outer primers F3 and B3 and a pair of inner primers FIP and BIP. These primers are specific, and hence they are capable of detecting and binding six different flanking regions of the target DNA sequence to be amplified. Starting from the 5'-end of the target DNA, the flanking regions are F3, F2, F1, B1c, B2c and B3c ("c" stands for complementary), The primers are so designed as to promote formation of hairpin-loop structures during the initial steps of the reaction, and consequently the synthesis of high amounts of self-primed DNA from such structures as the reaction proceeds.

In particular, outer primers F3 and B3 are normal single-domain primers and allow amplifying the whole target DNA sequence. The inner primers (FIP and BIP) are hybrid (double-domain) primers and consist of regions F1c and F2 (FIP) and regions B1c and B2 (BIP), respectively. Each primer in the inner pair is capable of recognising two out of the six regions of the target DNA and the pair of inner primers performs the main task in LAMP reaction (actually, they are used in a much higher concentration (in excess) than the pair of outer primers.

The LAMP reaction essentially includes two steps: a first step allows generating the starting structure for the actual amplification step, which is the second step.

In the first step, the inner primers react first. In particular, region F2 in FIP binds to the complementary region (F2c) of the target DNA and the elongation of the newly synthesised DNA strand by the polymerase begins.

At this point, outer primer F3 binds to the complementary region (F3c) of the target DNA and, by displacing the DNA strand synthesised starting from FIP, it releases the newly synthesised DNA strand. A loop structure is formed at the 3'-end of such a DNA strand, since region F1c (deriving from FIP) hybridises with region F1 of the newly synthesised strand.

Primers BIP and B3 react in similar manner on the other end.

At the end of this step, a target DNA is obtained, which is characterised by a structure (defined "self-structure") which self-hybridises at the ends thereby forming loops. Such a DNA will start the actual amplification step.

The self-structure is the new target DNA that, during the amplification step in LAMP, is amplified starting from primers FIP and BIP.

The amplification step begins with the elongation starting from the free 3' end of the self structure and with the elongation starting from FIP, which binds to loop region F2c. In this manner the same self-structure as that produced in the first step is formed again, together with a structure complementary thereto. The elongation reactions always continue starting from FIP and BIP until producing highly elongated structures. A further pair of primers, defined as loop forward (LF) and loop backward (LB) primers, may be added to the LAMP reaction mixture. Such primers aim at significantly accelerating the reaction, enabling a reduction even by 50% in the reaction time.

In the embodiment in which the synthesis and/or amplification of the nucleic acid is performed by using LAMP, the method of the present invention includes the steps of:
(i) providing at least one set of primers designed for amplifying at least one region of a target nucleic acid sequence by means of LAMP;
(ii) combining said set of primers with a reaction mixture for the amplification of a target nucleic acid by means of LAMP, said reaction mixture comprising at least one colorimetric metal indicator and at least one (bland) magnesium chelator;
(iii) placing the biological specimen in contact with the combination obtained from step (ii) so as to amplify at least one region of the target nucleic acid sequence possibly present in said specimen; and
(iv) verifying the possible change in the colour of the reaction mixture.

Steps (i) to (iv) just described may optionally be preceded by a step of nucleic acid denaturation. Preferably, said denaturation step is performed at a temperature of 90-100° C., for a time which preferably varies from 1 to 10 min, and more preferably from 4 to 8 min.

Also according to this embodiment, the addition of the combination of at least one colorimetric metal indicator and at least one bland magnesium chelator makes the reaction mixture colorimetrically sensitive to minimum amounts of amplified nucleic acid, which are capable of causing a definite change in the colour of the reaction mixture.

The synthesis and/or amplification reaction by means of LAMP is carried out at temperature which preferably varies from 50 to 80° C., and more preferably from 55 to 70° C.

The amplification reaction may be carried out in a thermostated bath and/or a stove and/or a thermal block.

The amplification reaction is made to proceed for a time which preferably varies from 30 to 90 min, and more preferably from 40 to 75 mM.

An aspect of the method of the present invention concerns the reaction mixture for nucleic acid amplification. The mixture preferably comprises: at least one polymerase; a buffer solution comprising a magnesium salt; a nucleotide triphosphate mixture; and/or at least one regulator of the melting temperature.

In the context of the present invention, the term "melting temperature" denotes the temperature at which half the nucleic acid is in the double helix (or double strand) condition and half is in the denatured (single strand) condition.

In general, the polymerase used in the method of the present invention is capable of amplifying the target nucleic acid (preferably, a DNA) preferably under isothermal conditions by means of a strand displacement activity.

In the context of the present invention, the term "strand displacement activity" denotes the ability of a polymerase to displace a nucleic acid strand, for instance a DNA molecule found downwards during the synthesis reaction, while leaving it integer (i.e. the term denotes the inability to hydrolyse the nucleic acid strand).

In particular, the polymerase is a DNA polymerase, preferably a thermophilic DNA polymerase. The big fragment of the thermophilic DNA polymerase of *Bacillus stearothermophilus* is particularly preferred for the aims of the present invention.

As to the buffer solution, it preferably comprises a magnesium salt, KCl, Tris-HCl, $NH_4SO_4$, triton X-100 and/or tween 20. Preferably, the magnesium salt is $MgSO_4$. Said magnesium salt is preferably employed in a concentration varying from 1 to 8 mM and, more preferably from 1.5 to 7 mM.

In particular embodiments of the invention it is possible to introduce further magnesium in the reaction mixture, for instance in the form of magnesium ion ($Mg^{2+}$), preferably by the addition of $MgCl_2$. In this respect, the Applicant has noticed that the use of magnesium, salified as a chloride, enhances the violet colour of the starting reaction mixture before the amplification reaction takes place.

As to the deoxynucleotide triphosphate mixture, it includes a mixture of dATP, dGTP, dCTP, dTTP, preferably in a concentration varying from 1000 μM to 3000 μM.

As to the melting temperature regulator, it is chosen from among: betaine, trimethylamine N-oxyde, proline, dimethylsulfoxide and formamide. The melting temperature regulator particularly preferred for the aims of the present invention is betaine, which is preferably used in a concentration varying from 0.6 M to 1.6 M.

As to the set of primers, it includes at least one pair of primers capable of recognising and binding the target nucleic acid sequence. The pair of primers preferably comprises a forward primer complementary to a sequence in the 5' region of the target nucleic acid and a reverse primer complementary to a sequence in the 3' region of the target nucleic acid.

In the embodiment in which the synthesis and/or amplification of the nucleic acid is performed by using LAMP, the set of primers of step (i) comprises at least one pair of inner primers and at least one pair of outer primers. Optionally, also the use of further pair of primers, defined as loop primers, can be provided for. Each pair of inner primers comprises at least one forward inner primer (FIP) and at least one reverse inner primer (BIP); each pair of outer primers comprises at least one forward outer primer (F3) complementary to F3c and at least one reverse outer primer (B3); each pair of loop primers comprises at least one inner loop primer (LF) and at least one outer loop primer (LB). Each primer in the set is designed so as to preferably form structures defined as "hairpin loops" during the first steps of the LAMP reaction.

Each inner primer is any arbitrarily selected nucleic acid sequence. For designing said sequence, it is preferable to consider that:
  the length of said sequence preferably varies from 35 to 60 nucleotides, more preferably from 40 to 60 nucleotides;
  the melting temperature of said sequence preferably varies from 55 to 70° C., more preferably from 52 to 63° C.;
  the GC percentage (i.e. the percentage guanine+cytosine content of said sequence with respect to the total nucleotide content) preferably varies from 30 to 65%, more preferably from 35 to 55%;

the concentration in which said sequence (i.e. each inner primer) is used preferably varies from 0.2 to 2 mM, more preferably from 0.6 to 1.6 mM.

Each outer primer is any arbitrarily selected nucleic acid sequence. For designing said sequence, it is preferable to consider that:

the length of F1c or B1c preferably varies from 20 to 30 nucleotides, more preferably from 17 to 22 nucleotides;

the length of F2 and B2 preferably varies from 20 to 30 nucleotides, more preferably from 17 to 22 nucleotides;

the melting temperature of F1c or B1c preferably varies from 63 to 68° C., more preferably from 52 to 63° C.;

the melting temperature of F2 or B2 preferably varies from 56 to 65° C., more preferably from 58 to 63° C.;

the GC percentage (i.e. the percentage guanine+cytosine content of said sequence with respect to the total nucleotide content) preferably varies from 30 to 65%, more preferably from 35 to 55%; and the concentration in which each outer primer is used preferably varies from 0.1 to 2 mM, more preferably from 0.1 to 1 mM.

Each loop primer is any nucleic acid sequence arbitrarily selected from among the sequences complementary to the sequences between F2 and F1c and B2 and B1c. For designing said sequence, it is preferable to consider that:

the length of said sequence preferably varies from 12 to 36 nucleotides, more preferably from 17 to 22 nucleotides;

the melting temperature of said sequence preferably varies from 55 to 70° C., more preferably from 52 to 63° C.;

the percentage GC (i.e. the percentage guanine+cytosine content of said sequence with respect to the total nucleotide content) preferably varies from 30 to 65%, more preferably from 35 to 55%; and the concentration in which said sequence (i.e. each loop primer) is used varies from 0.2 to 2 mM, preferably from 0.3 to 1 mM.

A further aspect of the present invention concerns the use of the method of the present invention in the health field, in particular for human health. Moreover, the method of the invention can be applied in the agricultural and food field and/or in the veterinary field.

Us of the method described above for detecting the presence of pathogens in a specimen is particularly preferred for the aims of the present invention. In this embodiment, what is being synthesised and/or amplified is a nucleic acid (DNA and/or RNA) belonging (specific) to the pathogen.

In particular, at least one pathogen is selected from among: *Mycoplasma, Listeria, Leptospira, Pseudomonas* or Parvovirus The pathogen belonging to the *Mycoplasma* genus preferably is a haemotropic *mycoplasma*. More preferably, said haemotropic *mycoplasma* is selected from among: *Candidatus Mycoplasma haemominutum, Candidatus Mycoplasma turicensis, Mycoplasma haemofelis, Mycoplasma haemocanis* and *Mycoplasma haematoparvum*.

The pathogen belonging to the *Listeria* genus is preferably *Listeria monocytogenes*.

The pathogen belonging to the *Leptospira* genus is preferably *Leptospira interrogans*.

The pathogen belonging to the *Pseudomonas* genus is preferably *Pseudomonas fluorescens*.

The pathogen of viral origin is preferably selected from among: canine Parvovirus (CPV) and feline panleukopenia virus (FPV).

As set forth above, in the context of this embodiment, the term "detecting the presence of at least one pathogen" means synthesising and/or amplifying at least one fragment of nucleic acid specific to the pathogen of interest. In other words, the method of the present invention includes in this case the synthesis and/or amplification of a region of the genome of the concerned pathogen by using specific primers.

Said synthesis and/or amplification may be carried out by means of LAMP, PCR or variants thereof. Preferably, the synthesis and/or amplification is carried out by means of LAMP.

Also in this embodiment, as described above, the synthesis and/or amplification reaction by means of LAMP is carried out at a temperature which preferably varies from 50 to 80° C., and more preferably from 55 to 70° C. The amplification reaction may be carried out in a thermostated bath and/or a stove and/or a thermal block.

The amplification reaction is made to continue for a time which preferably varies from 30 to 90 min, and more preferably from 40 to 75 min.

In case the synthesis and/or amplification of at least one fragment of nucleic acid of the concerned pathogen is carried out by means of LAMP, the design of each primer according to step (i) is carried out by taking into account what has been described above for the synthesis and/or amplification of the nucleic acid carried out by means of LAMP.

In particular, in the context of the present embodiment:

the at least one forward inner primer is preferably selected from among SEQ ID NO: 3, 9, 15, 21, 27, 33 and 39;

the at least one reverse inner primer is preferably selected from among SEQ ID NO: 4, 10, 16, 22, 28, 34 and 40;

the at least one forward outer primer is preferably selected from among SEQ ID NO: 1, 7, 13, 19, 25, 31 and 37, the at least one reverse outer primer is preferably selected from among SEQ ID NO: 2, 8, 14, 20, 26, 32 and 38.

Preferably, the pair of inner primers comprises SEQ ID NO: 3 and 4 or SEQ ID NO: 9 and 10 or SEQ ID NO: 15 and 16 and is specific for the detection of haemotropic mycoplasmas in dogs and cats.

Preferably, the pair of inner primers comprises: SEQ ID NO: 3 and 4 for the detection of *Candidatus Mycoplasma haemominutum*; SEQ ID NO: 9 and 10 for the detection of *Candidatus Mycoplasma turicensis*; SEQ ID NO: 15 and 16 for the detection of *Mycoplasma haemofelis*.

Preferably, the pair of inner primers includes SEQ ID NO: 21 and 22 and is specific for the detection of *Listeria* genus, preferably for the detection of *Listeria monocytogenes* species.

Preferably, the pair of inner primers includes SEQ ID NO: 39 and 40 and is specific for the detection of *Leptospira* genus, preferably for the detection of *Leptospira interrogans* species.

Preferably, the pair of inner primers includes SEQ ID NO: 33 and 34 and is specific for the detection of *Pseudomonas* genus, preferably for the detection of *Pseudomonas fluorescens* species.

Preferably, the pair of inner primers includes SEQ ID NO: 27 and 28 and is specific for the detection of Parvovirus genus, preferably for the detection of canine Parvovirus (CPV) and/or the detection of feline panleukopenia virus (FPV).

Preferably, the pair of outer primers comprises SEQ ID NO: 1 and 2 or SEQ ID NO: 7 and 8 or SEQ ID NO: 13 and 14 and is specific for the detection of *Mycoplasma* genus.

Preferably, the pair of outer primers comprises: SEQ ID NO: 1 and 2 for the detection of *Candidatus Mycoplasma haemominutum*; SEQ ID NO: 7 and 8 for the detection of *Candidatus Mycoplasma turicensis*; SEQ ID NO: 13 and 14 for the detection of *Mycoplasma haemofelis*.

Preferably, the pair of outer primers includes SEQ ID NO: 19 and 20 and is specific for the detection of *Listeria* genus, preferably for the detection of *Listeria monocytogenes* species.

Preferably, the pair of outer primers includes SEQ ID NO: 37 and 38 and is specific for the detection of *Leptospira* genus, preferably for the detection of *Leptospira interrogans* species.

Preferably, the pair of outer primers includes SEQ ID NO: 31 and 32 and is specific for the detection of *Pseudomonas* genus, preferably for the detection of *Pseudomonas fluorescens* species.

Preferably, the pair of outer primers includes SEQ ID NO: 25 and 26 and is specific for the detection of Parvovirus genus, preferably for the detection of canine Parvovirus (CPV) and/or the detection of feline panleukopenia virus (FPV).

In particular embodiments, the set of primers to which the present invention refers further includes a pair of loop primers.

Preferably, the pair of loop primers comprises: SEQ ID NO: 5 and 6, SEQ ID NO: 11 and 12; SEQ ID NO: 17 and 18; SEQ ID NO: 23 and 24; SEQ ID NO: 29 and 30; SEQ ID NO: 35 and 36; or SEQ ID NO: 41 and 42.

In a preferred embodiment, the pair of loop primers comprises: SEQ ID NO: 5 and 6, SEQ ID NO: 11 and 12; or SEQ ID NO: 17 and 18 and is specific for the detection of *Mycoplasma* genus.

Preferably, the pair of loop primers comprises: SEQ ID NO: 5 and 6 for the detection of *Candidatus Mycoplasma haemominutum*; SEQ ID NO: 11 and 12 for the detection of *Candidatus Mycoplasma turicensis*; SEQ ID NO: 17 and 18 for the detection of *Mycoplasma haemofelis*.

In a preferred embodiment, the pair of loop primers includes SEQ ID NO: 23 and 24 and is specific for the detection of *Listeria* genus, preferably for the detection of *Listeria monocytogenes* species.

In a preferred embodiment, the pair of loop primers includes SEQ ID NO: 41 and 42 and is specific for the detection of *Leptospira* genus, preferably for the detection of *Leptospira interrogans* species.

In a preferred embodiment, the pair of loop primers includes SEQ ID NO: 35 and 36 and is specific for the detection of *Pseudomonas* genus, preferably for the detection of *Pseudomonas fluorescens* species.

Preferably, the pair of loop primers includes SEQ ID NO: 29 and 30 and is specific for the detection of Parvovirus genus, preferably for the detection of canine Parvovirus (CPV) and/or the detection of feline panleukopenia virus (FPV).

The sequences to which the preferred embodiments of the present invention refer are listed in Table I.

TABLE I

| Species | Name | Sequence | SEQ ID NO |
|---|---|---|---|
| Candidatus Mycoplasma haemominutum | F3 | 5'-TTACCGAGGCTTGTAA TCTTTTGC-3' | SEQ ID NO: 1 |
| Candidatus Mycoplasma haemominutum | B3 | 5'-TGAGATAGGTTTTCGG TGATTAGCT-3' | SEQ ID NO: 2 |
| Candidatus Mycoplasma haemominutum | FIP | 5'CGCTCGTTACGGGACTT AACCAAACTGGAGGTTATC AGAATGACAGGTG-3' | SEQ ID NO: 3 |
| Candidatus Mycoplasma haemominutum | BIP | 5'TCGTAAGATATAGGAAG GCTGGGGCCATTATGCCTA CCATTGTAGCACG-3' | SEQ ID NO: 4 |
| Candidatus Mycoplasma haemominutum | LF | 5'-AGCTGACGACAGCCAT GCA-3' | SEQ ID NO: 5 |
| Candidatus Mycoplasma haemominutum | LB | 5'-CAAGTCATCATGCCCC TTATGCC-3' | SEQ ID NO: 6 |
| Candidatus Mycoplasma turicensis | F3 | 5'-AGGCGAAAACTTAGGC CATT-3' | SEQ ID NO: 7 |
| Candidatus Mycoplasma turicensis | B3 | 5'-TGTTCCACCACTTGTT CAGG-3' | SEQ ID NO: 8 |
| Candidatus Mycoplasma turicensis | FIP | 5'ACGGTGTGGACTACTGG GGTATTTTACGCTTAGGCT TGAAAGTGTG-3' | SEQ ID NO: 9 |
| Candidatus Mycoplasma turicensis | BIP | 5'TCGGCGTTGTAGCTTAC GTGTTTTTTTCCCCGTCAA TTCCTTTGAGT-3' | SEQ ID NO: 10 |
| Candidatus Mycoplasma turicensis | LF | 5'-TCTAATCCCATTTGCT ACC-3' | SEQ ID NO: 11 |
| Candidatus Mycoplasma turicensis | LB | 5'-CGCCTGGGTAGTACAT ATGC-3' | SEQ ID NO: 12 |
| Mycoplasma haemofelis | F3 | 5'-ATGAATGTATTTTTAA ATGCCCAC-3' | SEQ ID NO: 13 |
| Mycoplasma haemofelis | B3 | 5'-AAGGATGGGATCACGT CAAG-3' | SEQ ID NO: 14 |
| Mycoplasma haemofelis | FIP | 5'-ACCATCGCTGGTTTGC AACACATTTTGTCATCATG CCCCTTATGCC-3' | SEQ ID NO: 15 |
| Mycoplasma haemofelis | BIP | 5'TCGGATAGGAGGCTGCA ATTCGCCCCCGATATAGCT GACACGG-3' | SEQ ID NO: 16 |
| Mycoplasma haemofelis | LF | 5'-GCACGTTTGCAGCCCA A-3' | SEQ ID NO: 17 |
| Mycoplasma haemofelis | LB | 5'-CTCCTTGAAGTTGGAA TCACTAG-3' | SEQ ID NO: 18 |
| Listeria monocytogenes | F3 | 5'-AGCCGTGGATGTTATC GT-3' | SEQ ID NO: 19 |
| Listeria monocytogenes | B3 | 5'-GAAAAGCTTATTCATG GGG-3' | SEQ ID NO: 20 |
| Listeria monocytogenes | FIP | 5'-GTACGTGGAAGGGAGA TACCCTTTTTTGATTGCTC TGGTTACACT-3' | SEQ ID NO: 21 |
| Listeria monocytogenes | BIP | 5'-TGAATCTCAAGCAAAA CCTGGTTTTTCAACGTGAG AAATTCCGCTA-3' | SEQ ID NO: 22 |

TABLE I-continued

| Species | Name | Sequence | SEQ ID NO |
|---|---|---|---|
| Listeria monocytogenes | LF | 5'-GCTTTAGCAAATACAT ATTT-3' | SEQ ID NO: 23 |
| Listeria monocytogenes | LB | 5'-GATTTAGTATTCTTCG ACTATGG-3' | SEQ ID NO: 24 |
| CPV/FPV | F3 | 5'-CAGGTGATGAATTTGC TACAG-3' | SEQ ID NO: 25 |
| CPV/FPV | B3 | 5'-TCCTGCTGCAATAGGT GTT-3' | SEQ ID NO: 26 |
| CPV/FPV | FIP | 5'CCAAAGTTAGTACCTCC TTCAGCTTTTA CAAATA GAGCATTGGGCTT-3' | SEQ ID NO: 27 |
| CPV/FPV | BIP | 5'GACGTGGTGTAACTCAA ATGGGAATTTTGTGCACTA TAACCAACCTCAG-3' | SEQ ID NO: 28 |
| CPV/FPV | LF | 5'-GAGGCAAAGAATTTAG AAATGGTGG-3' | SEQ ID NO: 29 |
| CPV/FPV | LB | 5'-ACTGAAGCTACTATTA TGAGACCAG-3' | SEQ ID NO: 30 |
| Pseudomonas fluorescens | F3 | 5'-AAGCACTTTAAGTTGG GAGGA-3' | SEQ ID NO: 31 |
| Pseudomonas fluorescens | B3 | 5'-ACGCATTTCACCGCTA CAC-3' | SEQ ID NO: 32 |
| Pseudomonas fluorescens | FIP | 5'-TTACGCCCAGTAATTC CGATTAACGTTTTGACAGA ATAAGCACCGGCTAA-3' | SEQ ID NO: 33 |
| Pseudomonas fluorescens | BIP | 5'-CTCAACCTGGGAACTG CATTCAATTTTAGGAAATT CCACCACCCTCTA-3' | SEQ ID NO: 34 |
| Pseudomonas fluorescens | LF | 5'-CTGTATTACCGCGGCT GCTG-3' | SEQ ID NO: 35 |
| Pseudomonas fluorescens | LB | 5'-AACTGTCGAGCTAGAG TATGG-3' | SEQ ID NO: 36 |
| Leptospira interrogans | F3 | 5'-GTGGAATTCCAGGTGT AGC-3' | SEQ ID NO: 37 |
| Leptospira interrogans | B3 | 5'-GGTTTTTCGCGTATCA TCGA-3' | SEQ ID NO: 38 |
| Leptospira interrogans | FIP | 5'-ACCGGGGTATCTAATC CCGTTTTTTTTGCTGGCCT AAAACTGAC-3' | SEQ ID NO: 39 |
| Leptospira interrogans | BIP | 5'-AGTTGTTGGGGGTTTT AACCCTTTTTTTTCACTCT TGCGAGCATAG-3' | SEQ ID NO: 40 |
| Leptospira interrogans | LF | 5'-ACTACCCACGCTTTCG TGC-3' | SEQ ID NO: 41 |
| Leptospira interrogans | LB | 5'-ACGGATTAAGTAGACC GCCTG-3' | SEQ ID NO: 42 |

Nucleotide sequences characterised by 80-85% homology with respect to the above listed sequences are to be considered as utilisable in the method of the present invention.

The specimen that is subjected to the method of the present invention is any source of nucleic acid (DNA and/or RNA). In preferred embodiments, the specimen is any source of at least one pathogen or of the genome of at least one pathogen, for instance a food, water or soil.

Preferably the specimen is a biological specimen, for instance blood and its derivatives (plasma, serum and so on), urine or any biological fluid, a fragment of a tissue, hairs, faeces or cells.

The specimen can be used as such, or it can be subjected to lysis.

The lysed specimen will contain the nucleic acid of interest.

The lysate can be further purified in order to separate the nucleic acid molecule from the other components of the specimen.

As discussed above, the step of placing the reaction mixture for the nucleic acid amplification described above in contact with the specimen is necessary to prime the start of the reaction of synthesis and/or amplification of the target nucleic acid sequence possibly present in the specimen.

At the end of the reaction of amplification of the target nucleic acid sequence possibly present in the specimen, the change in the colour of the reaction mixture can be observed only if the synthesis and/or amplification of said sequence has taken place. When the method of the present invention is applied, the change in the colour of the reaction mixture is more definite and more apparent than in the prior art methods. Actually, the colour of the reaction mixture changes from a colour falling in the range of violet (for instance violet, lilac or magenta) to a colour falling in the range of blue (for instance, sky blue), whereas, by applying the prior art methods, the colour of the reaction mixture changes from a deep blue colour (before the amplification) to a sky blue colour (after amplification) or from magenta-violet to violet. The definite change in the colour of the reaction mixture that is observed by amplifying a nucleic acid in accordance with the present method is related to the addition of at least one colorimetric metal indicator and at least one bland magnesium chelator into the reaction mixture, as described above. The combined use of at least one colorimetric metal indicator and at least one bland magnesium chelator also has the advantage that it possibly allows using nucleotide triphosphate concentrations lower than those normally used in the prior art methods. For instance, the nucleotide concentrations may vary from 500 to 3000 µM, more preferably 1500 to 2000 µM. The method of the present invention thus allows visualising and/or monitoring the amplification of a nucleic acid by the naked eye (visually), as a change in the colour of the reaction mixture. Also a scarcely exercised or non-skilled viewer can ascertain whether or not the amplification of the nucleic acid sequence of interest has taken place at the end of the reaction, since the change in the colour of the reaction mixture is definite and apparent even when only minimum amounts of the sequence have been amplified.

As described before, the possibility of using lower nucleotide concentrations than those normally used in the prior art methods allows a considerable reduction in the costs for carrying out the method, since nucleotide triphosphates are very expensive. Hence, the method of the present invention is also very advantageous from an economic standpoint.

Usually, in order to monitor the reaction quality, that is, for instance, in order to check whether the reaction has correctly taken place, or whether or not the reactants being used work, or whether a contamination of the reactants occurs, one or more positive controls and/or one or more negative controls are employed.

In the context of the present method, therefore, a specimen may be a positive control or a negative control.

A positive control is, for instance, at least one region of the sequence of the nucleic acid of interest (target nucleic acid). Such a region can be the sequence of the region of the target nucleic acid as such (alone), for instance the double-stranded DNA sequence of the region. In the alternative, such a sequence may be inserted into any cloning vector. The cloning vector containing the sequence of at least one region of the target nucleic acid can be used as a positive control of the method of the present invention. In particular embodiments, the region considered, both in the form of a nucleotide sequence as such and in the form in which the nucleotide sequence of the region is inserted into a cloning vector, may be a region of the genome of a pathogen, in particular a region of the nucleic acid sequence of the pathogen being the target of the method of the present invention.

A positive control specimen, subjected to the method of the present invention, will take, at the end of the amplification reaction (whether it is a PCR or a LAMP) a sky blue colour. Hence, the specimen will change from a colour falling in the range of violet (before the amplification) to a colour falling in the range of blue, for instance, sky blue (after amplification), which will be indicative of the positive result of the method, that is of the quality of the reactant and the experimental conditions.

A negative control is a specimen where all reactants needed for the execution of the method are present, but no nucleic acid to be amplified is present. Therefore, the specimen will have the same colour both before and after amplification, that is, it will have a violet colour only if the method has correctly occurred (for instance, if there is no contamination).

In other words, by using at least one positive control and at least one negative control, the reliability of the method can be monitored.

In order to validate and/or confirm in quick and simple manner the result obtained by applying the method of the present invention it is possible to use the usual nucleic acid visualisation techniques available to any person of skill in the art: for instance, increase in turbidity, gel and UV race, fluorescence increase due to bonds of intercalating agents or fluorophore substances excited by UV-rays or by light of suitable wavelength.

A further aspect of the present invention concerns a kit for carrying out the method as described in the present patent application.

Said kit preferably comprises the following reactants:
  at least one set of primers according to the present invention;
  at least one buffer solution comprising a magnesium salt;
  at least one nucleotide triphosphate mixture;
  at least one polymerase;
  at least one melting temperature regulator;
  at least one colorimetric metal indicator;
  at least one bland magnesium chelator;
  at least one positive control;
  at least one negative control.

The kit components listed above are as described in the description of the method of the present invention. Moreover, the kit of the present invention may comprise different reaction tubes, preferably tubes of plastic material, of Eppendorf type. More preferably, the capacity of said tubes is in the range 0.2 to 0.5 ml.

The reaction tubes contain the reactants, which preferably are freeze-dried so that they can be preserved to ambient temperature.

In particular, the kit according to the present invention is used for the detection of the presence of a haemotropic *mycoplasma*, preferably selected from among: *Candidatus Mycoplasma haemominutum*, *Candidatus Mycoplasma turicensis*, *Mycoplasma haemofelis*, *Mycoplasma haemocanis* and *Mycoplasma haematoparvum*, in a biological specimen.

The kit of the invention is also used for the detection of a pathogen belonging to the *Listeria* genus, preferably *Listeria monocytogenes*, in a biological specimen.

The kit of the invention is also used for the detection of a pathogen belonging to the *Leptospira* genus, preferably *Leptospira interrogans*, in a biological specimen.

The kit of the invention is also used for the detection of a pathogen belonging to the *Pseudomonas* genus, preferably *Pseudomonas fluorescens*, in a biological specimen.

The kit of the invention is also used for the detection of a pathogen of viral origin, preferably selected from among canine Parvovirus (CPV) and feline panleukopenia virus (FPV), in a biological specimen.

In the preferred cases mentioned above, the kit according to the invention includes the primer sets as disclosed in the description of the method.

Example 1

Hydroxynaphthol blue is used in the LAMP methods in order to follow the amplification reaction according to the methods known in the art (Goto M et al., Biotechniques, 2009; Ma X J et al., J. Virol. Methods, 2010; Cardoso T C et al., Mol. Cell. Probes, 2010). The Applicant, when applying the prior art methods, has obtained a blue colour of the reaction mixture, before the LAMP amplification, which colour has not always enabled colorimetrically following the amplification reaction of the nucleic acid of interest. This is because, by applying the prior art methods, the amplification reaction has a deep blue colour before the amplification of the nucleic acid and, at the end of a possible amplification of the nucleic acid of interest, has a pale blue colour which seldom can be distinguished in definite manner from the colour of the starting mixture. FIG. 1A shows a positive specimen and a negative specimen when the method of Goto et al. is applied. We remind that a positive specimen provides information about a specimen where the nucleic acid has been amplified, and hence it provides an idea of the reaction mixture colour at the end of the amplification when the amplification of a nucleic acid occurred. A negative specimen provides information about a specimen where the nucleic acid has not been amplified, and hence it provides an idea of the starting colour of the reaction mixture, i.e. before amplification.

In order to enhance the colorimetric difference of the reaction mixture before and after the amplification of the possible nucleic acid, so as to enable a simple and fast monitoring of the same amplification even by non-skilled staff, a bland magnesium chelator has been added to the mixture. The bland magnesium chelator used is sodium citrate. It has been tested at the following concentrations: 0.25, 0.5, 0.75, 1, 1.25, 1.50, 1.75, 2, 2.5, 3, 4.5 mM.

The addition of sodium citrate and hydroxynaphthol blue to the reaction mixture for the LAMP amplification has given, before amplification, a violet colour to the mixture.

At the end of the possible amplification of the nucleic acid, the mixture has taken a sky blue colour, that can be clearly distinguished from the starting colour of the reaction mixture (before amplification).

FIG. 1B shows a positive specimen and a negative specimen when the method of the present invention is applied. The results show that the method of the present invention allows considerably enhancing the colour difference between the beginning and the end of the reaction if compared to the methods known in the literature.

In order to verify the actual functionality of sodium citrate in enhancing the contrast between the violet colour of the negative specimens and the sky blue colour of the positive specimens, a real time thermal cycler has been used.

SYBR GREEN has been used as the reading channel. Indeed, the Applicant has surprisingly found that, under these experimental conditions, the thermal cycler is capable of reading both the results of a conventional LAMP amplification, and the results of a LAMP to the reaction mixture of which hydroxynaphthol blue has been added.

Figure 2:
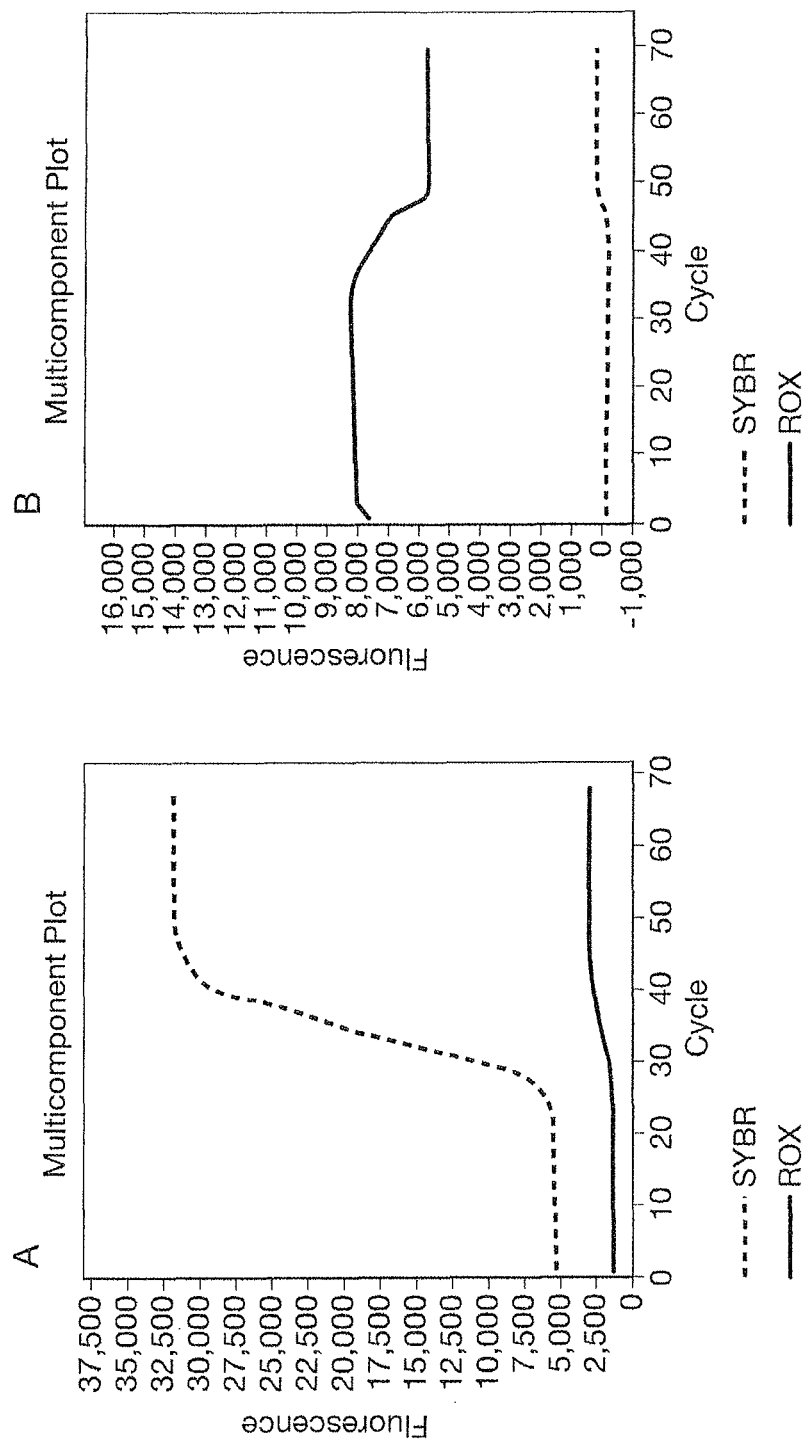
FIG. 2A shows, highlighted in grey, the increasing behaviour of a typical curve of a target DNA amplification by means of a LAMP reaction conducted in the presence of SYBR GREEN (which is the signal reading channel) by means of a real-time thermal cycler.
FIG. 2B shows, highlighted in black, the decreasing behaviour of the curve of a target DNA amplification by means of a LAMP reaction conducted in the presence of hydroxynaphthol blue (the signal reading channel used corresponds to the channel for SYBR GREEN) by means of a real-time thermal cycler.

In the presence of hydroxynaphthol blue, the curve corresponding to the amplification of the target DNA, instead of having an increasing behaviour as in the conventional LAMP (see FIG. 2A), has a decreasing behaviour as the colouring agent in the reaction mixture is changing from a violet colour to a sky blue colour (see FIG. 2B).

The experimental work has been divided into two steps, a first step of validation of the reading method described above, and a second step of evaluation of the effect of the addition of sodium citrate to the LAMP reaction mixture.

As to the first step of validation of the reading method of the results by means of a real time thermal cycler, 10 specimens containing the LAMP reaction mixtures with hydroxynaphthol blue (in 10 different tubes) and 10 specimens with the LAMP reaction mixtures containing SYBR SAFE have been prepared.

A same amount of a positive control (5 corresponding to about 90,000 targets) with the same dilution has been added to the specimens.

The specimens have been incubated for one hour at 65° C.

The curves of the two specimen pools (i.e. the reaction mixture with and without hydroxynaphthol blue) have been compared.

The two kinds of specimens have shown an increasing behaviour (in the case of the curve of the LAMP with SYBR SAFE) and a decreasing behaviour (in the case of the curve of the LAMP with hydroxynaphthol blue) in the amplification curve for the same number of cycles (see FIGS. 2A-B). Also the behaviours of the curves for both kinds of specimens have been identical (both curves attain the plateau at the same number of cycles).

This result has allowed determining that the real time thermal cycler can be used as a "non standard" instrument for reading the colour of a LAMP reaction mixture to which hydroxynaphthol blue has been added.

Figure 3:
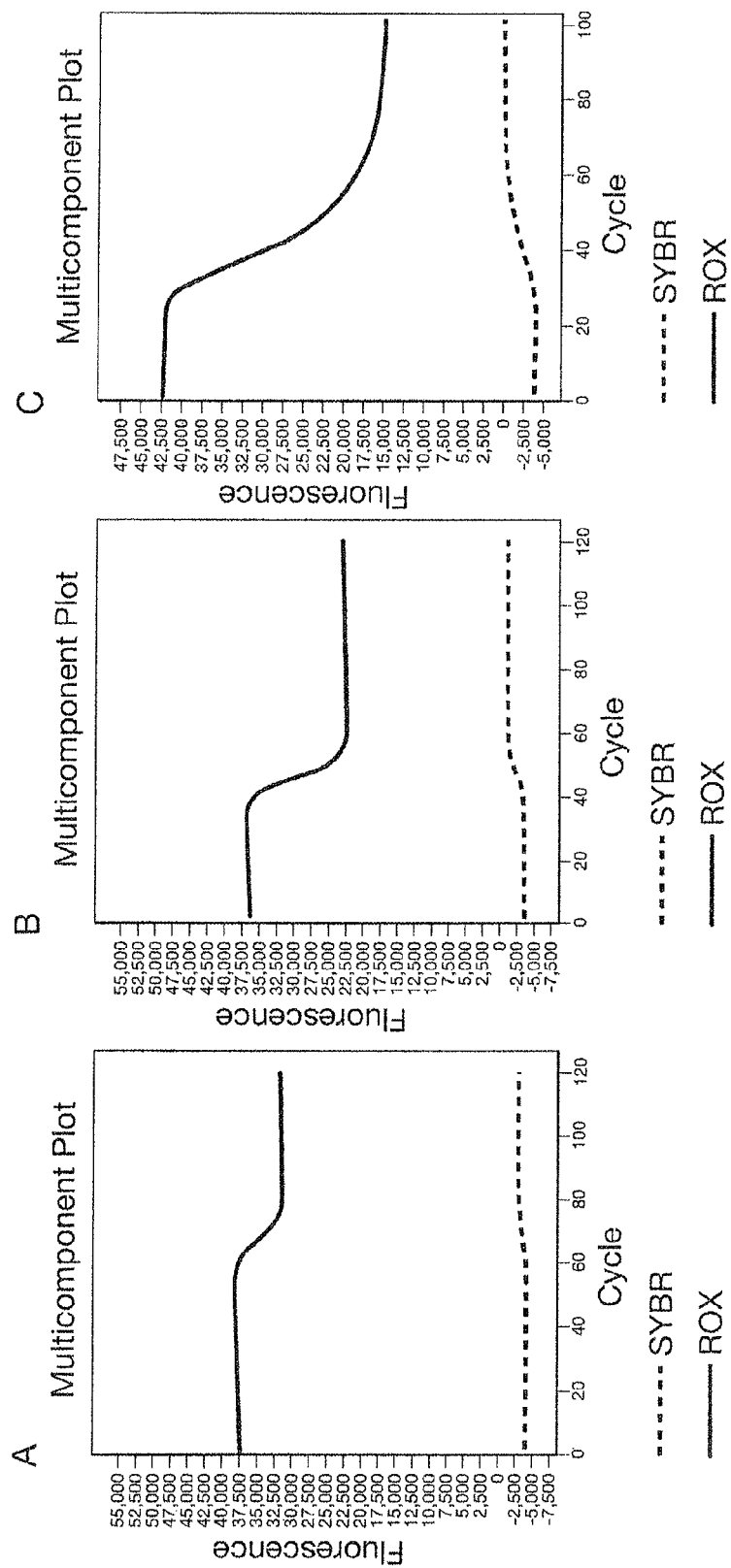
FIGS. 3A-3C show the effect of sodium citrate on the behaviour of the curve of amplification of a target DNA by means of a LAMP reaction conducted in the presence of SYBR SAFE and read in the SYBR GREEN channel in a real-time thermal cycler. The sodium citrate concentrations analysed are: 0.5 mM (FIG. 3A), 1 mM (FIG. 3B) and 1.5 mM (FIG. 3C).

The second step has included verifying the effect of sodium citrate on the change of colour of the LAMP reaction mixture. In particular, three LAMP reaction mixtures have been prepared, to which hydroxynaphthol blue and sodium citrate in increasing concentrations have been added. The concentrations of sodium citrate being analysed are: 0.5 mM (FIG. 3-A), 1 mM (FIGS. 3-B) and 1.5 mM (FIG. 3-C).

The same amount of a positive control (9,000 targets) has been added to each of the three mixtures.

The specimens have been incubated at 65° C. for 1 hour. The behaviours of the amplification curves at the three different concentrations of sodium citrate (see FIGS. 3 A-B.-C) show that the gap between the signal measured at the beginning of the amplification reaction and the end signal is the greater the higher the sodium citrate concentration in the mixture. The reaction has been inhibited by 5 mM concentrations.

These results have demonstrated that sodium citrate, in the positive specimens (i.e. in the tubes where the nucleic acid has been amplified) is effective in making the end colour of the reaction mixture tend to sky blue. Moreover, the addition of sodium citrate to the LAMP reaction mixture containing hydroxynaphthol blue has proved capable of enhancing the contrast between the negative specimens (i.e. the specimens of which the colour remains violet because the nucleic acid has not been amplified) and the positive specimens (i.e. the specimens of which the colour becomes sky blue because the nucleic acid has been amplified). In effect, with the method of the present invention, the colour difference between a positive and a negative specimen [violet (negative)–blue (positive)] is much more definite and detectable than in the method of Goto et al., which does not include the addition of sodium citrate [deep blue (negative)–sky blue (positive)]. The visual results are reported in FIG. 1, where FIG. 1A shows the specimens to which the prior art colorimetric method, which does not include a step of adding hydroxynaphthol blue in combination with sodium citrate to the LAMP reaction mixture, has been applied, whereas FIG. 1B shows the specimens to which the method of the present invention has been applied.

It is clearly apparent that, when applying the method of Goto et al. (FIG. 1A), the colour difference between a positive and a negative specimen is less distinguishable than when applying the method of the present invention (FIG. 1B).

Example 2

In order to demonstrate that sodium citrate does not inhibit the LAMP amplification reaction, the Applicant has subjected specimens containing a positive control (*Mycoplasma haemofelis, Candidatus Mycoplasma haemominutum, Candidatus Mycoplasma turicensis, Listeria monocytogenes, Leptospira interrogans, Pseudomonas fluorescens*, Parvovirus as control have been tested) to LAMP amplification reaction with and without sodium citrate.

In particular, 4 specimens containing 4 mM and 6 mM of magnesium with and without 1.5 mM of sodium citrate have been prepared.

Specifically, the samples are:
SAMPLE 1: LAMP reaction mixture containing 4 mM of magnesium;
SAMPLE 2: LAMP reaction mixture containing 4 mM of magnesium, 1.5 mM of sodium citrate;
SAMPLE 3: LAMP reaction mixture containing 6 mM of magnesium;
SAMPLE 4: LAMP reaction mixture containing 6 mM of magnesium, 1.5 mM of sodium citrate;

The LAMP has been conducted for 70 min at 65° C. and the results obtained (in minutes) are reported in the following table.

|  | Non-diluted specimen | Specimen with 1:10 dilution | Specimen with 1:20 dilution |
| --- | --- | --- | --- |
| Specimen 1 | 23.8 | 26.3 | 41.04 |
| Specimen 2 | 21.49 | 24.09 | 25.92 |
| Specimen 3 | 25.82 | 26.09 | 50.56 |
| Specimen 4 | 22.64 | 25.67 | 34.39 |

Each specimen has been tested as such and with 1:10 and 1:20 dilutions.

As it can be appreciated from the time values obtained, the specimens containing sodium citrate have lower values, that is, they develop the reaction more rapidly. Hence, it is deduced that the addition of sodium citrate does not inhibit the LAMP amplification reaction and, instead, in some cases, such addition can favour the reaction.

Example 3

Detection of Contamination with *Mycoplasma*

In order to test the validity of the method, specimens of DNA extracted from complete cat blood have been amplified by the method of the present invention in order to check whether the same were contaminated with the following pathogens: *Mycoplasma haemofelis, Candidatus Mycoplasma turicensis* and *Candidatus Mycoplasma haemominutum*.

The DNA has been extracted from the blood samples by using the commercial kit NucleoSpin® Tissue (Macherey-Nagel).

The detection of the possible specimen contamination has been verified by applying the method of the present invention and by using PCR.

Twenty specimens have been tested and the results obtained are as follows:

Results obtained by applying PCR:
  *Candidatus Mycoplasma haemominutum:* 9 positive specimens (of which 2 positive also for *Mycoplasma haemofelis* and 2 positive also for *Candidatus Mycoplasma turicensis*);
  *Candidatus Mycoplasma turicensis:* 2 positive specimens (2 of which positive also for *Candidatus Mycoplasma haemominutum*);
  *Mycoplasma haemofelis:* 3 positive specimens (2 of which positive also for cMhm);
  Negative specimens: 10.

Results obtained by applying the method of the invention:
  *Candidatus Mycoplasma haemominutum:* 9 positive specimens (of which 2 positive also for *Mycoplasma haemofelis* and 2 positive also for *Candidatus Mycoplasma turicensis*);
  *Candidatus Mycoplasma turicensis:* 2 positive specimens (2 of which positive also for *Mycoplasma* haemominutum);
  *Mycoplasma haemofelis:* 3 positive specimens (2 of which positive also for *Mycoplasma haemominutum*);
  Negative specimens: 10.

The following methods have been compared for the detection of the results obtained by the method of the present invention:
a) real time monitoring on a thermal cycler;
b) colour change with hydroxynaphthol with and without sodium citrate.

In the whole, 20 comparative tests have been carried out.

The two detection methods have shown a 100% congruence of the results only when the combination of hydroxynaphthol blue and sodium citrate is added to the reaction mixture, according to the method of the present invention.

Detection of Contamination with *Listeria monocytogenes*

In order to detect *Listeria monocytogenes,* 19 specimens of DNA extracted from bacterial cultures of *Listeria monocytogenes* have been tested. The DNA has been extracted by using the commercial kit NucleoSpin® Tissue (Macherey-Nagel).

The following methods have been compared for the detection of the results obtained by the method of the present invention:

a) real time monitoring on a thermal cycler;
b) colour change with hydroxynaphthol with and without sodium citrate.

In the whole, 20 comparative tests have been carried out.

The two detection methods have shown a 100% congruence of the results only when the combination of hydroxynaphthol blue and sodium citrate is added to the reaction mixture, according to the method of the present invention.

Moreover, tests have been carried out on a plasmid (in particular, vector pCR™4-TOPO® has been used as the plasmid), into which a DNA fragment has been introduced that corresponds to the same region of the genome of *Listeria* as the one being amplified. Tests have been carried out by means of LAMP reaction at serial dilutions (on a base 10) of the plasmid, and a sensitivity of the LAMP test of 2 targets/µl (corresponding to the ninth dilution on base 10 of the starting plasmid) has been detected.

Detection of Contamination with *Pseudomonas fluorescens*

In order to detect contamination with *Pseudomonas fluorescens,* 18 DNA specimens extracted from bacterial cultures of *Pseudomonas fluorescens* by using the commercial kit NucleoSpin® Tissue (Macherey-Nagel) have been tested.

The specimens have been subjected to the method of the invention and the occurred amplification has been verified both by means of real time monitoring and by means of colour change.

The results clearly show that only the method of the invention has been capable of detecting the presence of *Pseudomonas fluorescens* in all DNA specimens.

Detection of Contamination with *Leptospira*

In order to detect *Leptospira,* 11 DNA specimens extracted from urines (the positivity of which was known) by using the commercial kit NucleoSpin® Tissue (Macherey-Nagel) have been tested.

A double test has been carried out on the specimens, with the method of the present invention and with PCR.

The results have shown that the method of the present invention is capable of detecting 11 positives out of 11. The reference method PCR has detected 11 positives out of 11.

The method of the present invention has been carried out by visualising the results both by real time monitoring, and by using the change in the colour of the reaction mixture.

The two visualisation methods have shown a 100% congruence of the results.

Detection of Contamination with Parvovirus

In order to detect Parvovirus, 9 specimens of DNA extracted from faecal swabs (the positivity of which was known) by using the commercial kit NucleoSpin® Tissue (Macherey-Nagel) have been analysed.

The specimens have been analysed by means of PCR and by the method of the present invention, and the superimposability of the results has been verified.

Lastly, the step of detecting the product amplified according to the method of the present invention has been conducted both by using real time monitoring and by using the change in the colour of the reaction mixture. The results have shown a 100% congruence of the results obtained with both different methods.

The invention claimed is:

1. A method for detecting the synthesis and/or amplification of a target nucleic acid sequence, comprising the steps of:

(i) providing at least one set of primers designed for synthesising and/or amplifying at least one region of said target nucleic acid sequence;

(ii) combining the set of primers as per step (i) with a reaction mixture for the amplification of said at least one region of the target nucleic acid sequence, said reaction mixture comprising at least one colorimetric metal indicator and at least one magnesium chelator;

(iii) placing the reaction mixture obtained from step (ii) in contact with a biological specimen so as to amplify said at least one region of the target nucleic acid sequence possibly present in said specimen; and (iv) verifying a possible change in the colour of the reaction mixture, wherein said colorimetric metal indicator and said magnesium chelator are hydroxynaphthol blue and sodium citrate, respectively.

2. The method according to claim 1, wherein said possible change in colour of the reaction mixture is from a colour falling in the range of violet, lilac or magenta, to a colour falling in the range of blue.

3. The method according to claim 1, wherein said method of synthesis and/or amplification of a nucleic acid sequence is LAMP.

4. The method according to claim 3, wherein step (i) comprises the steps of:

(a) arbitrarily selecting a sequence F3c, a sequence F2c and a sequence F1c in the 3' region of the target nucleic acid sequence starting from the 3' end;

(b) arbitrarily selecting a sequence B3, a sequence B2 and a sequence B1 in the 5' region of the nucleic acid sequence starting from the 5' end;

(c) providing at least one set of primers in order to amplify said target nucleic acid sequence by LAMP, said set comprising:

(c1) at least one pair of inner primers comprising a forward inner primer (FIP) and a reverse inner primer (BIP), said FIP comprising a sequence F2 complementary to F2c and the sequence F1c complementary to F1, said BIP comprising the sequence B2 complementary to B2c and a sequence B1c complementary to B1;

(c2) at least one pair of outer primers comprising a forward outer primer (F3) complementary to F3c and a reverse outer primer (B3) corresponding to the region B3c of said target nucleic acid sequence.

5. The method according to claim 4, wherein the set of primers as per step (c) further comprises at least one pair of loop primers comprising an outer loop primer (LB) and an inner loop primer (FB).

6. The method according to claim 1, wherein the reaction mixture of said step (ii) comprises a deoxynucleotide triphosphate mixture at a concentration varying between 1000 and 3000 μM.

7. The method according to claim 1, further comprising detecting the presence of at least one pathogen selected from among: *Mycoplasma, Listeria, Leptospira, Pseudomonas*, canine Parvovirus (CPV) and feline panleukopenia virus (FPV) in a biological specimen.

8. The method according to claim 7, wherein said *Mycoplasma* is selected from among: *Candidatus Mycoplasma haemominutum, Candidatus Mycoplasma turicensis, Mycoplasma haemofelis, Mycoplasma haemocanis* and *Mycoplasma haematoparvum*; said *Listeria* is *Listeria monocytogenes*; said *Leptospira* is *Leptospira interrogans*; said *Pseudomonas* is *Pseudomonas fluorescens*.

9. The method according to claim 4, further comprising detecting the presence of at least one pathogen selected from among: *Mycoplasma, Listeria, Leptospira, Pseudomonas*, canine Parvovirus (CPV) and feline panleukopenia virus (FPV) in a biological specimen.

10. The method according to claim 9, wherein said *Mycoplasma* is selected from among: *Candidatus Myco-*

*plasma haemominutum, Candidatus Mycoplasma turicensis, Mycoplasma haemofelis, Mycoplasma haemocanis* and *Mycoplasma haematoparvum*; said *Listeria* is *Listeria monocytogenes*; said *Leptospira* is *Leptospira interrogans*; said *Pseudomonas* is *Pseudomonas fluorescens*.

11. The method according to claim 9, wherein for *Candidatus Mycoplasma haemominutum* said set of primers comprises the primers F3, B3, FIP, BIP, LF and LB having sequences corresponding to SEQ ID NO: 1, 2, 3, 4, 5 and 6, respectively; for *Candidatus Mycoplasma turicensis* said set of primers comprises the primers F3, B3 FIP, BIP, LF and LB having sequences corresponding to SEQ ID NO: 7, 8, 9, 10, 11 and 12, respectively; for *Mycoplasma haemofelis* said set of primers comprises the primers F3, B3, FIP, BIP, LF and LB having sequences corresponding to SEQ ID NO: 13, 14, 15, 16, 17 and 18, respectively; for *Listeria monocytogenes* said set of primers comprises the primers F3, B3, FIP, BIP, LF and LB having sequences corresponding to SEQ ID 10 NO: 19, 20, 21, 22 and 24, respectively; for canine Parvovirus (CPV) and feline panleukopenia virus (FPV) said set of primers comprises the primers F3, B3, FIP, BIP, LF and LB having sequences corresponding to SEQ ID 10 NO: 25, 26, 27, 28, 29 and 30, respectively; for *Pseudomonas fluorescens* said set of primers comprises the primers F3, B3, FIP, BIP, LF and LB having sequences corresponding to SEQ ID NO: 31, 32, 33, 34, 35 and 36, respectively; and for *Leptospira interrogans* aid set of primers comprises the primers F3, B3, FIP, BIP, LF and LB, having sequences corresponding to SEQ ID NO: 37, 38, 39, 40, 41 and 42, respectively.

12. The method according to claim 10, wherein for *Candidatus Mycoplasma haemominutum* said set of primers comprises the primers F3, B3, FIP, BIP, LF and LB having sequences corresponding to SEQ ID NO: 1, 2, 3, 4, 5 and 6, respectively; for *Candidatus Mycoplasma turicensis* said set of primers comprises the primers F3, B3, FIP, BIP, LF and LB having sequences corresponding to SEQ ID NO: 7, 8, 9, 10, 11 and 12, respectively; for *Mycoplasma haemofelis* said set of primers comprises the primers F3, B3, FIP, BIP, LF and LB having sequences corresponding to SEQ ID NO: 13, 14, 15, 16, 17 and 18, respectively; for *Listeria monocytogenes* said set of primers comprises the primers F3, B3, FIP, BIP, LF and LB having sequences corresponding to SEQ ID 10 NO: 19, 20, 21, 22 and 24, respectively; for canine Parvovirus (CPV) and feline panleukopenia virus (FPV) said set of primers comprises the primers F3, B3, FIP, BIP, LF and LB having sequences corresponding to SEQ ID 10 NO: 25, 26, 27, 28, 29 and 30, respectively; for *Pseudomonas fluorescens* said set of primers comprises the primers F3, B3, FTP, BIP, LF and LB having sequences corresponding to SEQ ID NO 31, 32, 33, 34, 35 and 36, respectively; and for *Leptospira interrogans* said set of primers comprises the primers F3, B3, FIP, BIP, LF and LB, having sequences corresponding to SEQ ID NO: 37, 38, 39, 40, 41 and 42, respectively.

13. A kit for carrying out the method in accordance with claim 1, comprising:
   a set of primers designed for synthesising and/or amplifying at least one region of a target nucleic acid sequence;
   at least one buffer solution comprising a magnesium salt;
   at least one nucleotide triphosphate mixture;
   at least one polymerase;
   at least one regulator of a melting temperature;
   hydroxynaphthol blue;
   sodium citrate;
   at least one positive control; and
   at least one negative control.

14. The method according to claim 1, wherein said possible change in colour of the reaction mixture is from violet to sky blue.

* * * * *